United States Patent

Sauceda et al.

[11] Patent Number: 5,997,549
[45] Date of Patent: Dec. 7, 1999

[54] WART REMOVING TOOL

[76] Inventors: Charles J. Sauceda, 1390 Flynn Rd., Unit H, Camarillo, Calif. 93012; Lynn A. Abel, 2714 Antonio Dr., Camarillo, Calif. 93010; Stanley B. Abel, P.O. Box 67, Somis, Calif. 93066

[21] Appl. No.: 09/250,911

[22] Filed: Feb. 16, 1999

[51] Int. Cl.⁶ .............................. A61F 29/04; A61F 44/00
[52] U.S. Cl. .................................... 606/131; 132/76.4
[58] Field of Search ................... 132/76.4, 75.6; 606/131

[56] References Cited

U.S. PATENT DOCUMENTS

| | | | |
|---|---|---|---|
| 454,956 | 6/1891 | Levy | 132/76.4 |
| 2,557,175 | 6/1951 | Cortes | 132/76.4 |
| 2,699,791 | 1/1955 | Hansen | 132/76.4 |
| 3,196,885 | 7/1965 | Emerson | 132/76.4 |
| 3,198,198 | 8/1965 | Bittner | 132/76.4 |
| 3,318,318 | 5/1967 | Gewirz | 132/76.4 |
| 3,809,101 | 5/1974 | Shimizu | 132/76.4 |
| 4,397,325 | 8/1983 | Van Roeyen | 132/76.4 |
| 4,537,207 | 8/1985 | Gilhaus | 132/76.4 |
| 4,712,552 | 12/1987 | Pangburn | 128/355 |
| 4,785,835 | 11/1988 | Bray | 132/76.4 |
| 5,053,024 | 10/1991 | Duoretzky | 604/291 |
| 5,082,009 | 1/1992 | Cromer | 132/76.4 |
| 5,088,509 | 2/1992 | Savage, III | 132/76.4 |
| 5,287,863 | 2/1994 | La Joie et al. | 132/76.4 |
| 5,361,786 | 11/1994 | Pangburn | 132/76.4 |
| 5,732,719 | 3/1998 | Godbout | 132/76.4 |

*Primary Examiner*—Paul J. Hirsch
*Attorney, Agent, or Firm*—Jack C. Munro

[57] ABSTRACT

A wart removing tool which comprises a carbide pad mounted at one end of an elongated handle. The carbide pad has an exterior substantially planar surface which is roughened by being knurled/serrated. The carbide pad is to include cobalt with the carbide being from the group consisting of iron carbide, manganese carbide, chromium carbide, molybdenum carbide, vanadium carbide, tantalum carbide, niobium carbide, titanium carbide and tungsten carbide. The tool is to be utilized by the roughened surface being rubbed against a wart at least twice a day with these rubbings occuring several hours apart. This type of application is to occur for period of time between four and ten weeks during which time the wart will diminish in size until gone from the body.

3 Claims, 1 Drawing Sheet

WART REMOVING TOOL

BACKGROUND OF THE INVENTION

1) Field of the Invention

The field of this invention relates to a medical type of device and more particularly to a device that can be used to effect removal of warts from an animal body, such as a human body.

2) Description of the Prior Art

A wart is defined as a papillomatous growth which occurs on the surface of the skin of an animal body with generally warts being common within humans. Warts are caused by a virus. Warts are deemed to be undesirable by being unattractive. In the past, there have been numerous lotions that have been designed to be appliable to the wart and, after a period of time, the wart is to drop off of the body. However, in the past, these lotions have proved to be rather ineffective and/or painful. Additionally, it is common to remove warts with an electric needle. The disadvantage of such an electric needle is that it destroys the wart by "burning" which produces a rather unslightly appearance until the area heals which was occupied by the wart. This burning also results in the creating of a permanent unsightly scar. Also, at times, this technique results in the wart regrowing not resulting in the elimination of the wart.

SUMMARY OF THE INVENTION

A wart removing tool which is defined by an elongated handle which terminates in an operating end. Mounted on the operating end is a carbide pad. The carbide pad could be from the group that includes iron carbide, manganese carbide, chromium carbide, molybdenum carbide, vanadium carbide, tantalum carbide, niobium carbide, titanium carbide and tungsten carbide. Also, it is believed to be important that the carbide include cobalt. The pad has an exterior substantially planar operating surface with this operating surface being roughened as by being knurled or serrated. The method of application of the tool is to rub the roughened surface of the carbide pad against the upper surface of the wart for a period of a few seconds. This rubbing is to occur at least two times a day, such as in the morning and in the evening. This type of application of the carbide pad to the wart is to occur until the wart actually diminishes in size until gone from the body with generally this application to proceed for between four and ten weeks. Preferably, the application of the tool is to occur after bathing when the wart is soft.

A primary objective of the present invention is to construct a wart removing tool which will effect removing of a wart by repeated rubbing applications applied to the surface of the wart over a period of time.

Another objective of the present invention is to produce removing of a wart in a painless and chemical free manner.

DETAILED DESCRIPTION OF THE PREFERRED EMBODIMENT

Figure 1:
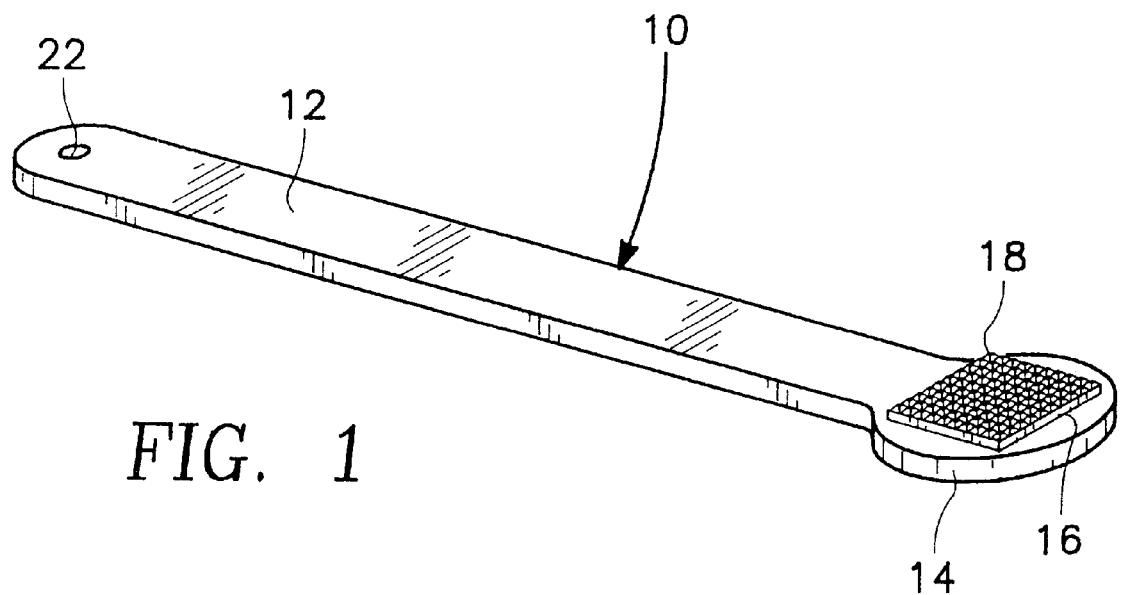
FIG. 1 is an isometric view of the wart removing tool of the present invention.
Figure 2:
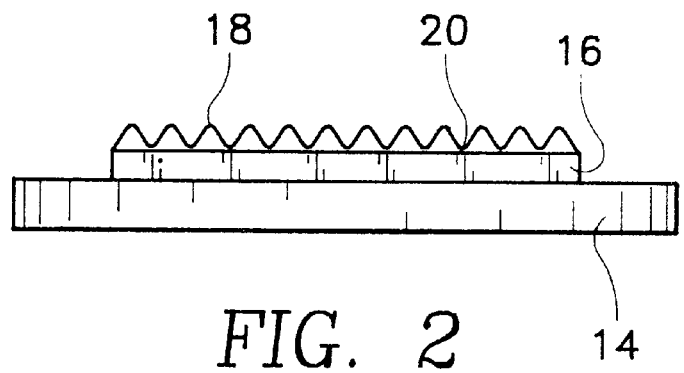
FIG. 2 is an end view of the wart removing tool of the present invention showing more clearly the carbide pad mounted in conjunction with the operating end of the wart removing tool. This figure is shown enlarged four times from what is shown in FIG. 1.

Referring particularly to the drawings, there is shown the wart removing tool 10 which has an elongated, thin handle 12 which is enlarged at one end thereof defining an operating end 14. Mounted on the operating end 14 is a carbide pad 16. The carbide pad 16 has a substantially planar operating surface 18 which is knurled or serrated defining a crisscross pattern of V-shaped grooves 20. The back end of the handle 12 includes a hole 22. The function of the hole 22 is to facilitate hanging of the tool 10 on some type of protuberance, such as a small nail or key ring, which is not shown. The carbide pad 16 will be generally adhesively attached to the operating end 14. The knurled/serrated operating surface 18 produces a roughened surface, and it is this roughened surface that will be applied against the upper surface of a wart, which is not shown. The applying of this roughened surface is by rubbing of the operating surface 18 in an oscillating manner against the upper surface of the wart. This rubbing is to occur for a period of time, such as a few seconds, at least twice a day with generally once being in the morning and then once in the evening each day for a period of time of between four to ten weeks until the wart actually diminishes in size until gone from the body.

The material of construction for the carbide pad is to be a carbide from the group consisting of an iron carbide, manganese carbide, chromium carbide, molybdenum carbide, vanadium carbide, tantalum carbide, niobium carbide, titanium carbide and tungsten carbide. If, for example, tungsten carbide is selected, the pad 16 will include tungsten carbide of between seventy-five and ninety-six percent by weight, cobalt between four and twenty-five percent by weight, nickel between zero and one percent by weight, vanadium carbide between zero and one percent by weight, tantalum carbide between zero and two percent by weight and niobium carbide between zero and one percent by weight.

A carbide is a binary compound of carbon with an element less electronegative of carbon. Most carbides are prepared by heating a mixture of the powdered metal, carbon and tungsten, usually to a high temperature, but not necessarily as high as the melting point of the tungsten and the carbon, and pressed into shapes (sintering process). Also, a carbide may be produced by heating a mixture of the oxide of the metal, carbon with tungsten.

The preferable time to apply the tool of the present invention is directly after bathing of the human. This will result in a softening of the wart, and when the abrasive, knurled/serrated operating surface 18 is applied to the wart, it will function to dig into the surface and penetrate a short distance into the upper layer of the wart. It is believed that this application causes an interaction between the carbide and possibly the cobalt contained within the carbide which functions to neutralize the virus that creates the wart.

What is claimed is:

1. A wart removing tool comprising:

an elongated handle terminating in an operating end; and a metallic pad affixed to said operating end, said pad having an exterior substantially planar surface, said exterior substantially planar surface being knurled/serrated, said metallic pad being constructed of carbide which includes cobalt, whereby upon rubbing of said pad for a few seconds upon a wart, which is located on a body, with the rubbing occurring a series of instances over a period of time will result in the wart dropping off of the body.

2. The wart removing tool as defined in claim 1 wherein:

said carbide being from the group consisting of iron carbide, manganese carbide, chromium carbide, molybdenum carbide, vanadium carbide, tantalum carbide, niobium carbide, titanium carbide and tungsten carbide.

3. The method of removing a wart attached to a body comprising the steps of:

utilizing a tool which has a knurled/serrated surface carbide pad which includes cobalt;

rubbing the carbide pad onto the wart in an oscillating manner for a few seconds in time with this rubbing to occur at least twice a day, spaced several hours apart, for a period of at least twenty-eight days; and extracting the wart by merely having the wart diminish in size until gone from the body without producing pain to the body.

* * * * *